United States Patent
Chao et al.

(10) Patent No.: US 7,012,986 B1
(45) Date of Patent: Mar. 14, 2006

(54) METHOD AND SYSTEM FOR CALIBRATING A COMPUTED TOMOGRAPHY SYSTEM

(75) Inventors: Edward Henry Chao, Oconomowoc, WI (US); Eric Matthew Plate, Waukesha, WI (US); Michael Ronald Miller, Waukesha, WI (US); Tara Janon Mahan, New Berlin, WI (US); Thomas John Myers, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/993,555

(22) Filed: Nov. 19, 2004

(51) Int. Cl.
*A61B 6/00* (2006.01)
(52) U.S. Cl. .......................................... 378/4; 378/207

(58) Field of Classification Search .................... 378/4, 378/21, 57, 62, 205, 207; 382/131, 132; 250/363.03
See application file for complete search history.

(56) References Cited

U.S. PATENT DOCUMENTS

6,561,695 B1  5/2003  Proksa .......................... 378/207

*Primary Examiner*—Edward J. Glick
*Assistant Examiner*—Courtney Thomas
(74) *Attorney, Agent, or Firm*—Carl B. Horton, Esq.; Armstrong Teasdale LLP (57) ABSTRACT

Methods and systems for calibrating a Computed Tomography (CT) system are provided. The method includes performing a CT scan of an object having a substantially flat surface using the CT system. The method further includes determining an offset angle for the CT system based on an image of the substantially flat surface of the scanned object.

19 Claims, 7 Drawing Sheets

METHOD AND SYSTEM FOR CALIBRATING A COMPUTED TOMOGRAPHY SYSTEM

BACKGROUND OF THE INVENTION

This invention relates generally to medical imaging systems, and more particularly, to methods and systems for calibrating a Computed Tomography (CT) system.

An increase in the precision of medical imaging and diagnosis has led to a need for even more precise calibration and alignment of medical imaging systems. For example, Radiation Therapy (RT) for oncology patients requires the patients to be positioned accurately on a CT scanner table and that the resulting CT images be rendered with good positional accuracy. In a CT system, lasers are used for accurate positional registration. Misalignment of lasers may affect the correct positioning of the patient on the table. This misalignment may affect the planning of treatments that require good positional accuracy in the reconstructed CT images. For example, in Radiation Therapy (RT) systems, even a small rotation of half a degree in the image is undesirable as it may have a significant effect on the treatment of a patient.

In a CT system, the rotational misalignment may be attributed to errors in the mechanical setup. Examples of errors in the mechanical setup include, but are not limited to, unleveled stationary base of the CT system, incorrect angular position of encoders on the gantry of the CT system, inaccuracy of the encoder pulse with respect to the encoder gear tooth, and the like. These inaccuracies result in the rotation of the final image with respect to the actual positioning of the object being scanned. These inaccuracies also result in the rotation of the positioning lasers.

Existing methods address these problems either on an ad-hoc basis or do not provide a robust solution.

BRIEF DESCRIPTION OF THE INVENTION

In an exemplary embodiment of the invention, a method for calibrating a computed tomography (CT) system is provided. The method includes performing a CT scan of an object having a substantially flat surface by using the CT system. The method further includes determining an offset angle for the CT system based on an image of the substantially flat surface of the scanned object.

In another exemplary embodiment of the invention, a computed tomography (CT) system is provided. The CT system includes a CT scanner having a rotatable gantry. The CT system further includes a offset unit for controlling the rotation of the gantry and is configured to receive an offset angle value to determine the rotational position of the gantry. The offset angle is based on an image of an object scanned by the CT scanner with the object having a substantially flat surface.

DETAILED DESCRIPTION OF THE INVENTION

Various embodiments of the invention provide for calibrating the rotational misalignment of a Computed Tomography (CT) system. More specifically, various embodiments of the invention provide rotational alignment of a CT system by removing inaccuracies that may arise due to the mechanical setup of the CT system. Examples of factors that lead to rotational misalignment in the mechanical setup include, but are not limited to, levelness of the stationary base, angular positioning of encoders, accuracy of encoder pulse relative to a particular position of the encoder gear tooth, among others. These inaccuracies may result in the rotation of the coronal and sagittal lasers from true vertical or true horizontal (as defined by gravity), and may also result in the rotation of the final image with respect to the actual positioning of the object being scanned. In general, in various embodiments of the invention, the calibration involves identifying from an image of, for example, a horizontal or vertical leveled surface, the amount of rotational error due to inaccuracies in the mechanical setup. These inaccuracies are then calibrated or corrected by compensating for the offset due to the rotational error. The calibration can be performed when the CT system is configured or when the need for calibration arises.

Figure 1:
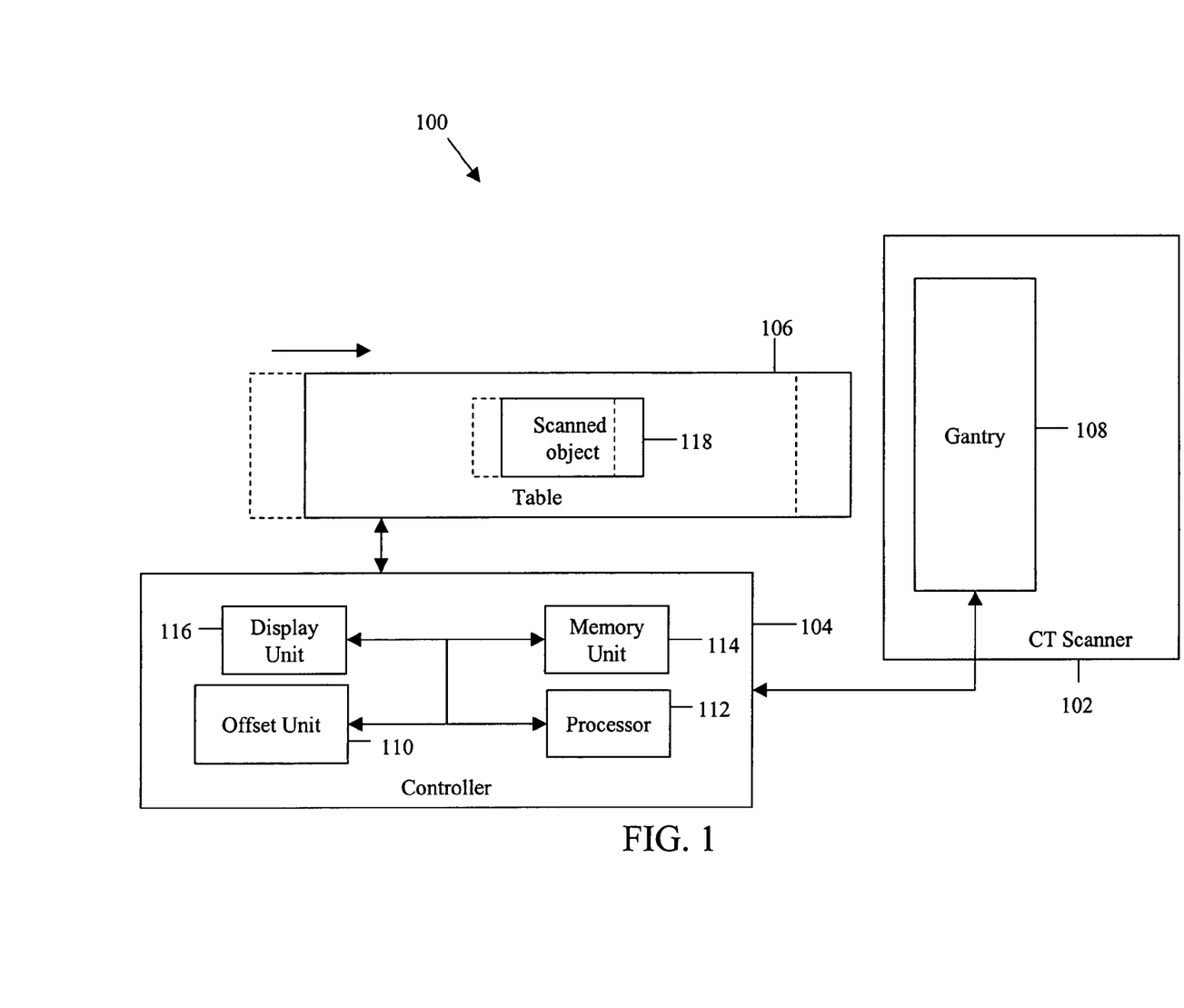
FIG. 1 is a block diagram of a computed tomography (CT) system in accordance with an exemplary embodiment of the invention.

FIG. 1 is block diagram of a CT system 100 according to an exemplary embodiment of the invention. CT system 100 includes a CT scanner 102, a controller 104, and a table 106. CT scanner 102 includes a gantry 108. Controller 104 includes a offset unit 110, a processor 112, a memory unit 114, and a display unit 116. A scanned object 118 is placed on table 106. In an exemplary embodiment of the invention, scanned object 118 is a leveled horizontal surface. CT scanner 102 through gantry 108 acquires image related data of scanned object 118, for example, in an incremental imaging process. This is provided by controlling the rotation of gantry 108 and the axial movement of table 106. Controller 104 controls the axial movement of table 106 and monitors the angular position of gantry 108. In operation, data is acquired as gantry 108 rotates and offset unit 110 labels each set of data with the gantry angle as described in more detail herein. The resultant data, and the angle at which the data is captured, are stored in memory unit 114 within controller 104. Processor 112 combines the resultant image related data, based on its angular location, to generate one or more images. Further, the generated images corresponding to a flat surface are used to compute rotational calibration values by computing the amount of angular misalignment. The rotational calibration values are communicated to offset unit 110, which offsets the labels of each set of data by the given amount in order to remove rotational misalignment in the subsequent images, as described in more detail herein.

In various embodiments of the invention, offset unit 110 is a firmware that interacts with processor 112 to remove rotational misalignments in gantry 108. In an exemplary embodiment, offset unit 110 is a controller board. In another embodiment, offset unit 110 is programmed to offset gantry angle values by an amount determined during calibration. Offset unit 110 sends corrected angular values to processor 112 that subsequently produces corrected images. Memory unit 114 may be a magnetic or an optical storage media, such as a hard disk, a tape drive, a compact disc (CD), or a memory chip. Memory unit 114 also may be other similar means for loading computer programs or other instructions into the computer system. Further, display unit 116 may include a cathode ray display, a LCD display, or a plasma display. Display unit 116 is used to display the image of scanned object 118. Display unit 116 is also used to determine the calibration values.

Figure 2:
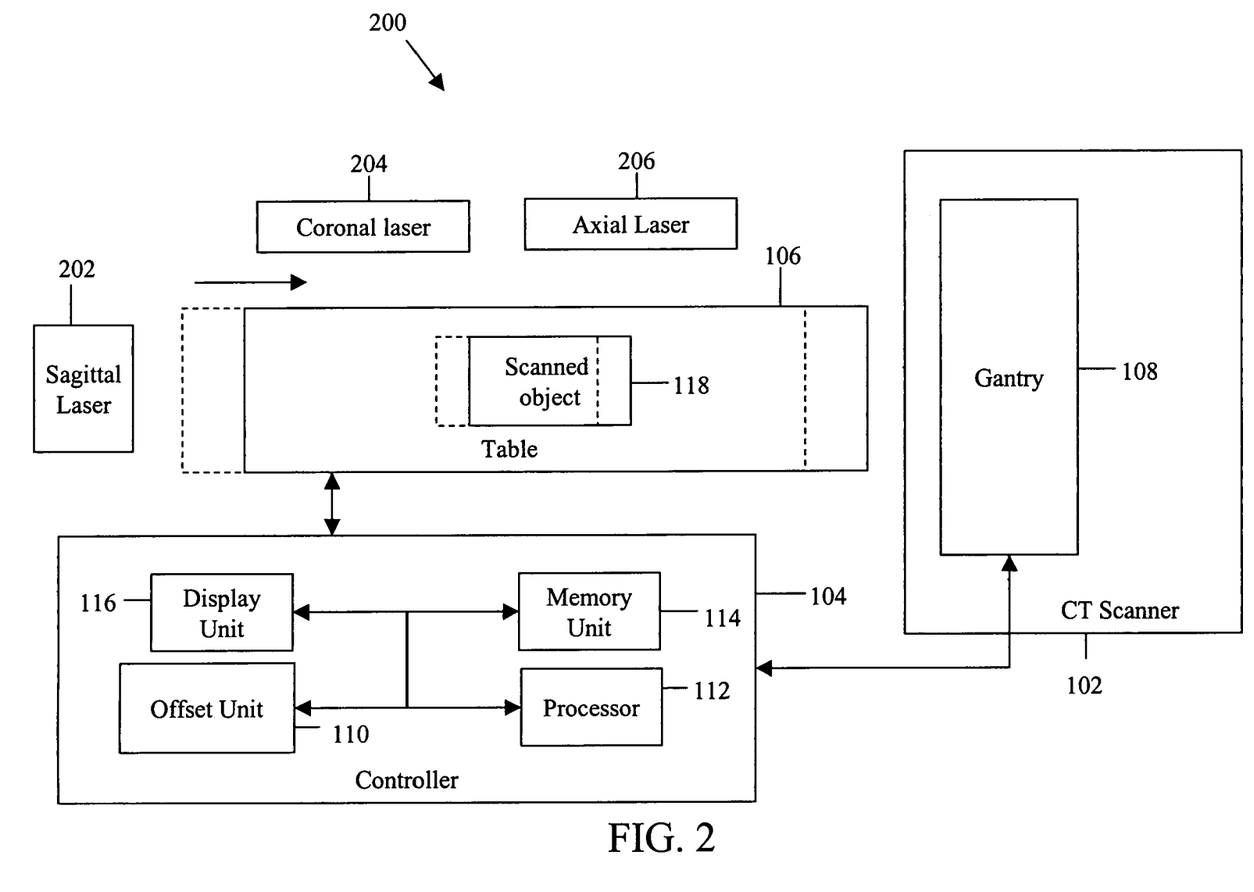
FIG. 2 is a block diagram of a CT system in accordance with another exemplary embodiment of the invention.

FIG. 2 is block diagram of a CT system 200 according to another exemplary embodiment of the invention. In addition to the components of CT system 100, CT system 200 includes a sagittal laser 202, a coronal laser 204, and an axial laser 206. The lasers are used in CT system 200 to align scanned object 118 at a correct location before the scan of scanned object 118 is performed. In CT system 200, sagittal laser 202 represents a computed tomographic imaging plane that positions scanned object 118 by using a longitudinal plane. The longitudinal plane splits the plane of the body of scanned object 118 into left and right portions. Coronal laser 204 represents a computed tomographic imaging plane that positions scanned object 118 by using a horizontal plane. The horizontal plane splits the plane of the body of scanned object 118 into top and bottom portions. Finally, axial laser 206 represents a computed tomographic imaging plane that positions scanned object 118 by using a vertical plane. The vertical plane splits the plane of the body of scanned object 118 into front and back portions. In addition to removing inaccuracies in the reconstruction of CT images, this embodiment of the invention enables calibration of CT system 200 to remove inaccuracies relating to misalignment of sagittal, and coronal lasers.

In various embodiments of the invention, sagittal laser 202, coronal laser 204, and axial laser 206 are provided inside scanner 102.

In should be noted that the various methods or various embodiments of the invention described below may be completed in connection with medical imaging systems other than CT system 100 or CT system 200, such as, for example, position emission tomography (PET)/CT dual modality system.

Figure 3:
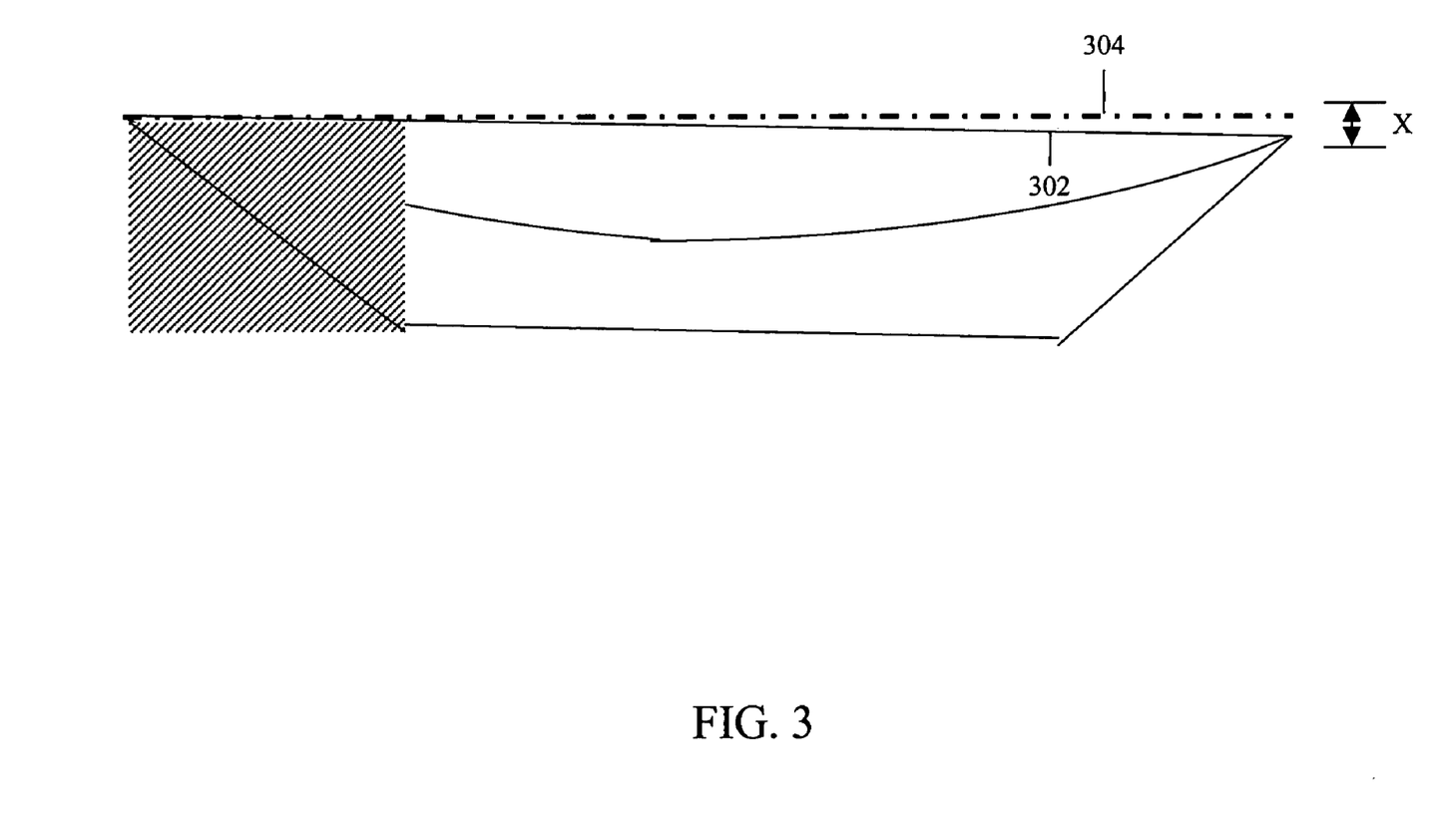
FIG. 3 is an exemplary illustration of computing an offset angle in accordance with an exemplary embodiment of the inventor.

FIG. 3 is an exemplary illustration of an image used to compute the rotational inaccuracy in the mechanical setup of CT system 200. The top surface of scanned object 302 is known to be substantially leveled. However, the reconstructed image of object 302 is shown to be non-level compared to a horizontal line 304. In order to determine the magnitude of this inaccuracy, referred to as angular error, the angle between the top surface of the reconstructed image of object 302 and horizontal line 304 is computed. In the present embodiment, the top surface of scanned object 302 is a flat horizontal surface or a substantially flat horizontal surface. However, the method can be extended to any flat surface with a known surface angle. Examples of flat surfaces include, but are not limited to, the surface of water in a container, a thread with a load at its end, a flat horizontal table, and the like. A flat surface is chosen to provide an image of a surface having a substantially flat plane. The images of table 106 are acquired using gantry 108 (shown in FIG. 2) and are controlled by controller 104 (shown in FIG. 2).

In an exemplary embodiment of the invention, processor 112 (shown in FIG. 2) generates an image of object 302 and horizontal line 304. The image is generated from an axial view. In an exemplary embodiment of the invention, horizontal line 304 may be generated by identifying pixel values related to the end of object 302. The offset angle is determined by computing the angular displacement between the surface of object 302 and horizontal line 304. The angular displacement may be computed, for example, by dividing the vertical distance 'X' in the level of the surface of object 302 and horizontal line 304, by the length of horizontal line 304. For example, if the difference in the level of the surface of object 302 and horizontal line 304 is −6.22 millimeters (mm) and the length of horizontal line 304 is 400 mm, the angular displacement is computed as arctan (−6.22/400)=−0.89 degrees. If the end of object 302 selected for generating horizontal line 304 is vertically above the other end, a negative sign of the angle indicates a downward tilt in the surface of table 106 and a positive sign of the angle represents an upward tilt in object 302. However, if the end of object 302 selected for generating horizontal line 304 is vertically below the other end, a negative sign of the angle indicates an upward tilt in object 302.

The offset angle is further used by offset unit 110 to label the location of scan position of gantry 108 with respect to scanned object 118. For example, in the example mentioned above, offset unit 110 adds 0.89 degrees to the zero scan position (zero degrees) of gantry 108 and every scan position thereafter. For the subsequent scans, offset unit 110, while labeling the zero scan position, adds 0.89 degrees to it. In this way, when gantry 108 performs a scan at 0.89 degrees it records the reading at 0.89 degrees as at the zero scan position. This ensures that the angle at which a scan needs to be performed and the corresponding angle registered in connection with that angle in memory unit 114, are identical. Subsequently, 0.89 degrees is added by offset unit 110 to the each scan position. For example, the data obtained at 2 degrees is registered as the data at 2.89 degrees. This corrects for the error caused due to rotational misalignment.

Figure 4:
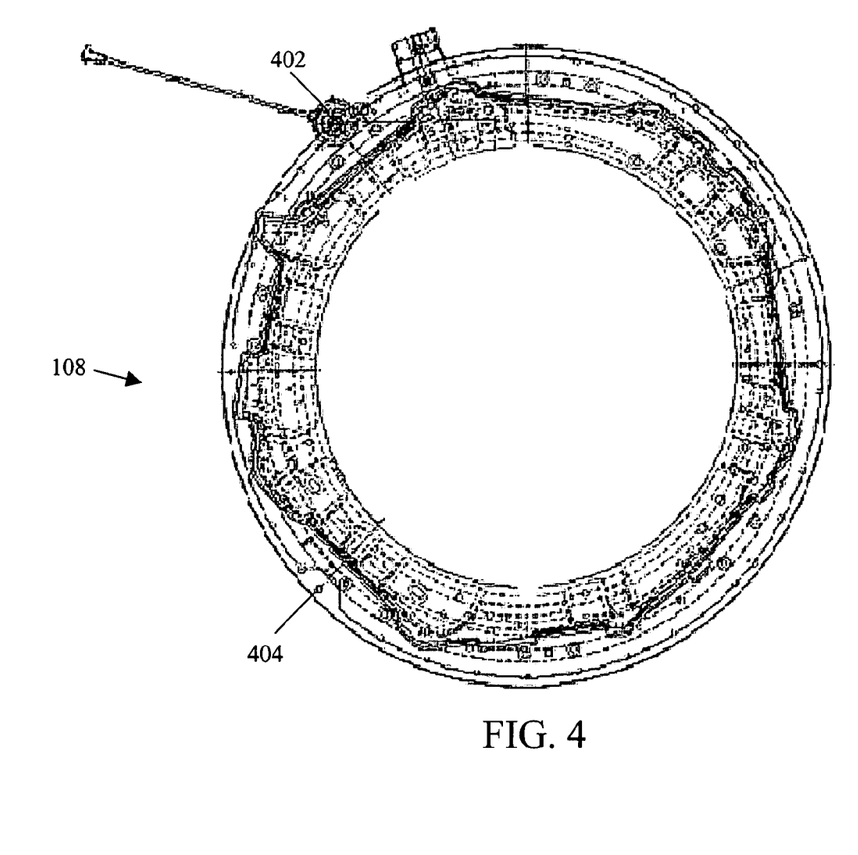
FIG. 4 is a diagram of a gantry of a CT system in accordance with an exemplary embodiment of the invention.

FIG. 4 is a diagram of gantry 108 (shown in FIG. 1) of CT system 100 and CT system 200. Gantry 108 includes an encoder 402 and an X-ray tube 404. Encoder 402 monitors the angular position of gantry 108 and communicates the angle, at which gantry 108 performs the scan, to offset unit 110. Encoder 402 communicates with gantry 108 by generating a signal when the gantry angle changes by a set amount. The signal is measured in terms of number of signals per degree. For example, encoder 402 may provide 106496 signals per gantry rotation (360°), i.e., 295.8 signals per degree. For example, corresponding to the −0.89 degrees of angular error computed in the example provided in connection with FIG. 3, a delay of 0.89*295.8=264 signals is provided. Offset unit 110 adds this number of signals (in terms of the offset angle) to the signal generated by encoder 402 in order to correct for inaccuracies in the setup of gantry. As a result of this change in each set of data obtained over 360 degrees, the reconstructed images is corrected for rotational misalignment. It should be noted that X-ray tube 404 emits X-ray radiations, wherein the intensity of the X-ray radiations may be controlled at X-ray source or by controller 104.

Figure 5:
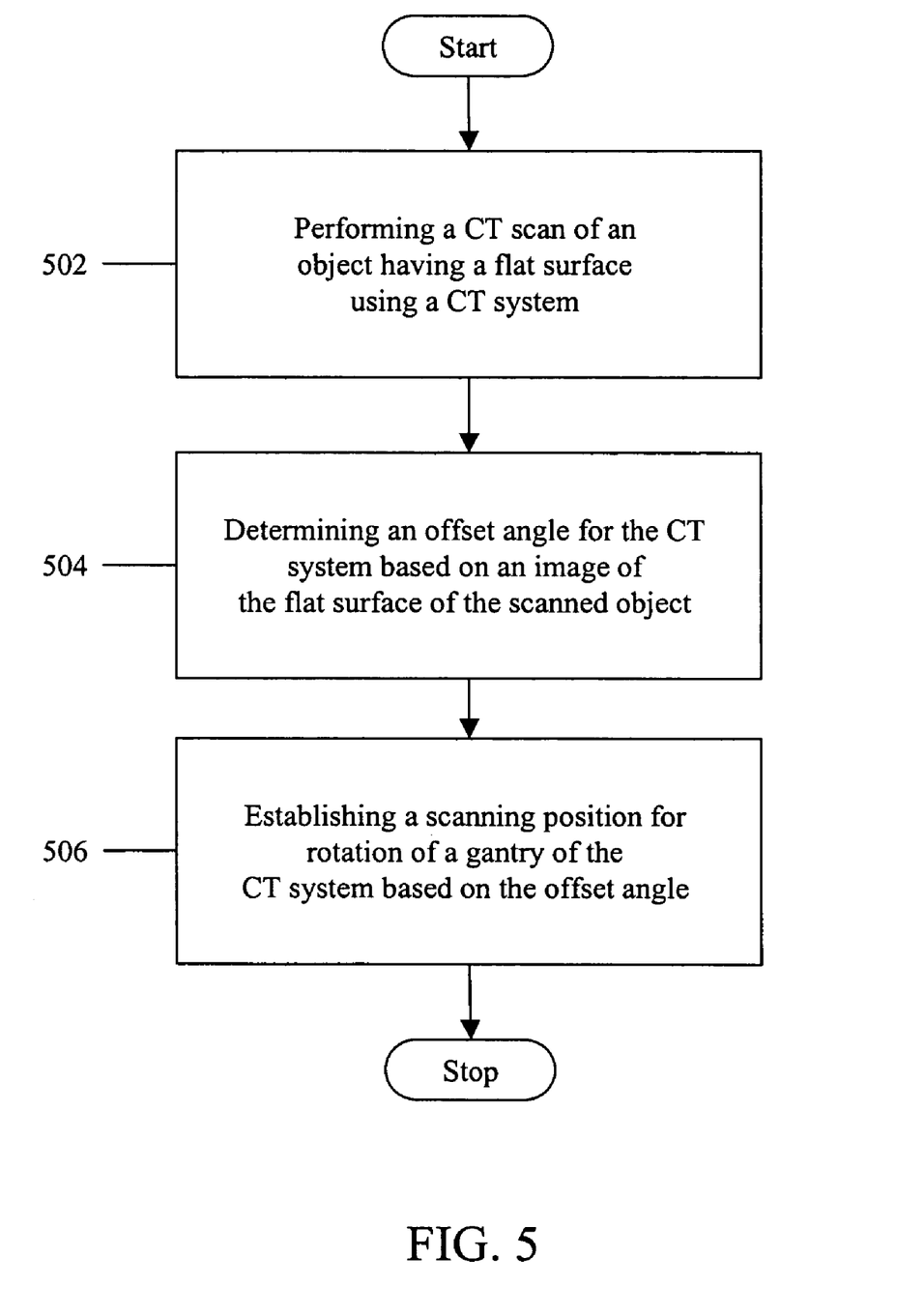
FIG. 5 is a flowchart for calibrating the rotational misalignment of a CT system in accordance with an exemplary embodiment of the invention.

FIG. 5 is a flowchart for calibrating CT system 100 and CT system 200 according to an exemplary embodiment of the invention. At 502, a CT scan of an object having a flat or substantially flat surface is performed. At 504, the offset angle of CT system 100 is determined. The offset angle is determined based on the image of the object having the flat or substantially flat surface. The image is acquired by CT system 100. The offset angle is computed as described herein in conjunction with FIG. 3. At 506, the offset angle is input into offset unit 110. In various embodiments, the offset angle may be represented in terms of encoder signals as described herein. Offset unit 110, while labeling each angle, adds this offset angle to the angle recorded by encoder 402 for all the data acquired. As a result of this change in the recorded angle, images are reconstructed without the rotational misalignment caused by gantry inaccuracies.

Figure 6A:
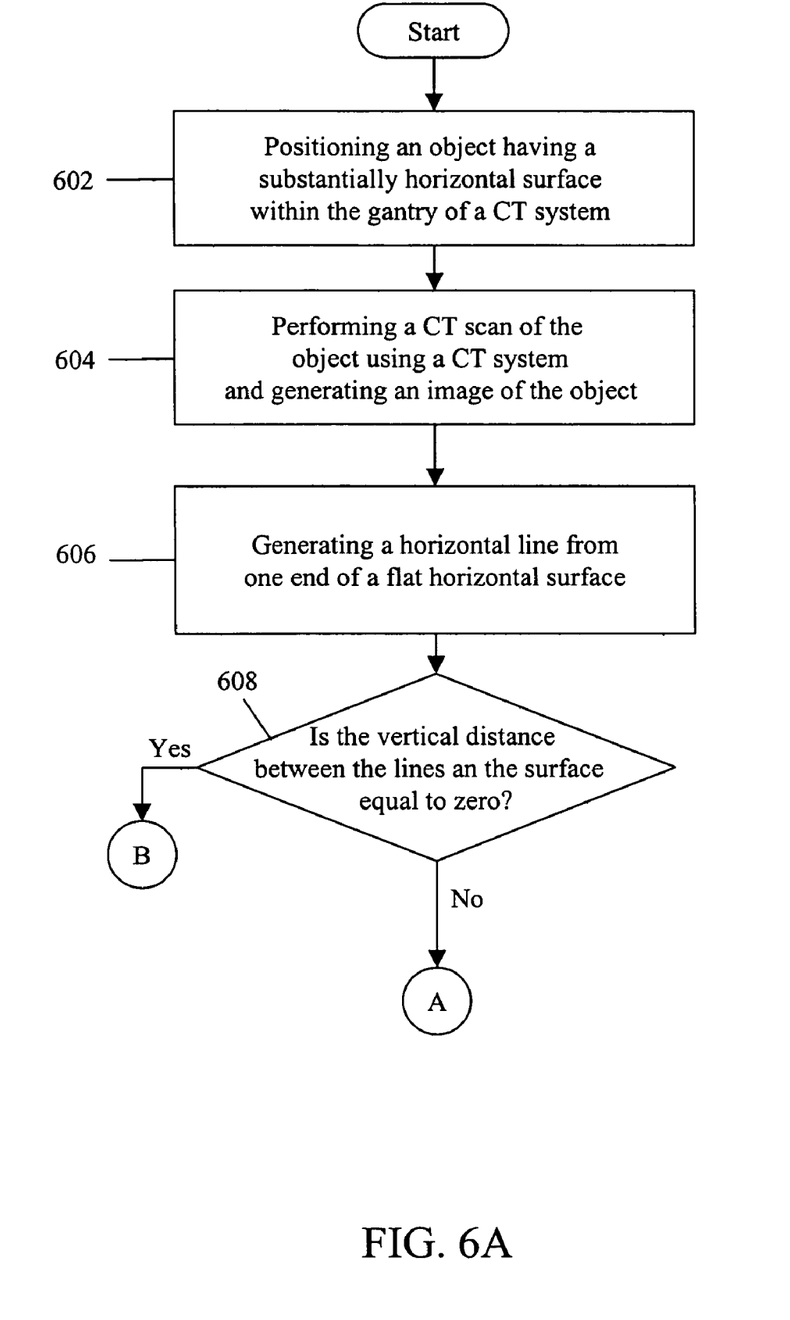
FIGS. 6A and 6B show a flowchart for calibrating the rotational misalignment of a CT system in accordance with another exemplary embodiment of the invention.
Figure 6B:
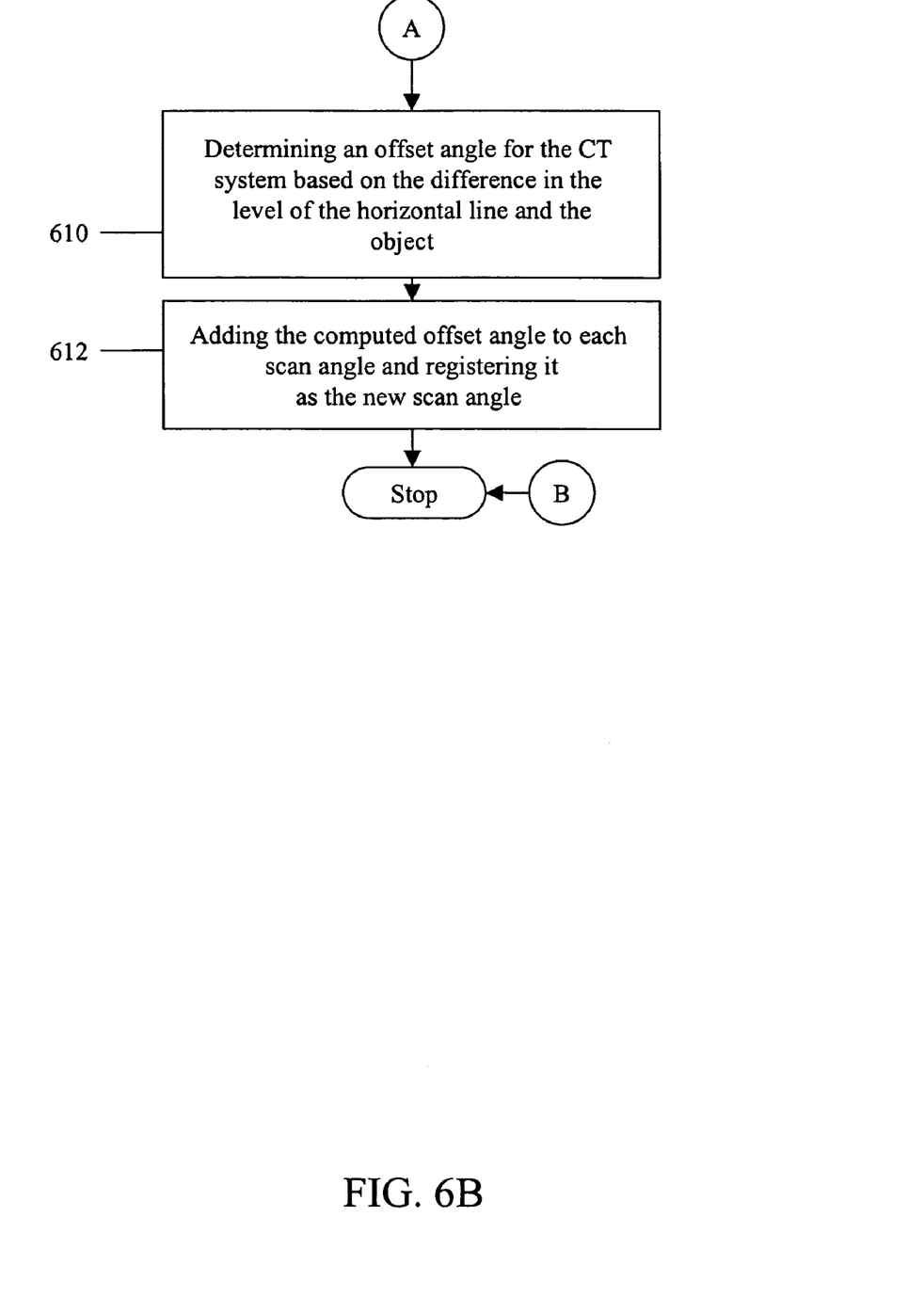

FIGS. 6A and 6B show a flowchart for calibrating the rotational misalignment in CT system 100 and CT system 200 according to another exemplary embodiment of the invention. At 602, an object having a flat or substantially flat (e.g., horizontal) surface is placed inside gantry 108 (shown in FIG. 1). In various embodiments, the object may be, for example, a container having water therein. At 604, a CT scan of the object is performed and one or more images of the object are generated. Controller 104 generates images using known methods of CT image reconstruction. At 606, processor 112 generates a horizontal line from one end of the object. At 608, processor 112 compares the vertical distance between the object and the horizontal line drawn from one end of the object. If the vertical distance is computed to be zero, the method terminates. If not, at 610, processor 112 determines the offset angle (as described in connection with FIG. 3) from the angular displacement between the two lines. At 612, the computed offset angle is entered into the offset unit 110. Offset unit 110, while labeling each image captured, adds the offset angle to the original angle and records the resultant angle as the labeled angle corresponding to that scan.

In various embodiments of the invention, the rotational misalignment may be removed iteratively. The offset angle computed at each iteration may be used to identify the rotational misalignment in the subsequent scans. These scans may then be further used to reduce the rotational misalignment in CT system 100 and CT system 200.

Thus, in various embodiments of the invention, the error in reconstructed image is corrected using the method described by the flowchart in FIG. 6A and FIG. 6B.

Various embodiments of the invention improve the positional accuracy of a generated image and the positional accuracy of the patient positioning lasers. The positional accuracy is improved by calibrating the angular position of the gantry. This calibration compensates, for example, for errors in the mechanical setup of the CT system.

Various embodiments of the invention enable improved combination of CT images with images generated from other types of medical imaging systems. For example, after calibrating the starting position of the gantry, the corrected CT image may be combined with a PET image.

Various embodiments of the invention enable accurate radiation treatment (RT) of oncology patients. RT requires accurate image generation for diagnosis and treatment. The images generated from a CT system controlled by various embodiments of the invention reduce or eliminate errors related to mechanical setup to provide more accurate images.

A technical effect of various embodiments of the invention is improved positional accuracy of an image. The positional accuracy is improved by calibrating the rotational misalignment of the gantry. Another technical effect of various embodiments of the invention is that CT images acquired after the calibration can more accurately be combined with images acquired from other medical imaging systems. Thus, these images can be combined without further processing.

The various embodiments of the invention and components thereof may be implemented as part of a computer system. The computer system may include a computer, an input device, a display unit and an interface, for example, for accessing the Internet.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer system executes a set of instructions that are stored in one or more storage elements, in order to process input data. The storage elements may also hold data or other information as desired or needed. The storage element may be in the form of an information source or a physical memory element within the processing machine.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While the invention has been described in terms of various specific embodiments, those skilled in the art will recognize that the invention can be practiced with modification within the spirit and scope of the claims.

What is claimed is:

1. A method for calibrating a computed tomography (CT) system, said method comprising:
   performing a CT scan of an object having a substantially flat surface using the CT system; and
   determining an offset angle for the CT system based on an image of the substantially flat surface of the scanned object.

2. A method in accordance with claim 1 further comprising establishing a scan starting position for rotation of a gantry of the CT system based on the offset angle.

3. A method in accordance with claim 1 wherein the substantially flat surface comprises a substantially horizontal flat surface.

4. A method in accordance with claim 3 wherein the substantially horizontal flat surface is defined by liquid within a container.

5. A method in accordance with claim 1 further comprising comparing the image of the substantially flat surface of the scanned object with an image of a substantially straight line to determine the offset angle.

6. A method in accordance with claim 5 wherein the image of the substantially straight line is defined by a plurality of generally horizontal pixels on a display of the CT system on which the image of the substantially flat surface of the scanned object, is displayed.

7. A method in accordance with claim 5 further comprising determining the offset angle based on a measured distance between an end of the image of the substantially flat surface and an end of the image of the substantially straight line.

8. A method in accordance with claim 1 further comprising adjusting the horizontal level of the image based on a measured level of the substantially flat surface.

9. A method according to claim 8, wherein the horizontal level of the image is adjusted by adding the offset angle to the angular output of the scan.

10. A method according to claim 9, wherein the offset angle is added to the angular output of the scan during the setup of the CT system.

11. A method in accordance with claim 1 wherein determining the offset angle is performed iteratively.

12. A method in accordance with claim 11 further comprising determining the levelness of the image of the substantially flat surface of the scanned object after each iteration to determine if another iteration is to be performed.

13. A method in accordance with claim 1 wherein images scanned by the CT system are configured for use in connection with a radiology treatment planning system.

14. A method in accordance with claim 1 wherein the CT system comprises a positron emission tomography (PET)/CT system.

15. A method for aligning a gantry of a computed tomography (CT) system, said method comprising:
    positioning an object having a substantially horizontal surface within the gantry of the CT system;
    performing a CT scan of the object using the CT system;
    comparing an image of the substantially horizontal surface of the object obtained by the CT scan and displayed on a display of the CT system with a substantially horizontal line displayed on the display; and
    determining an offset angle for the gantry based on a determined difference of horizontal levelness between the displayed substantially horizontal surface and the displayed substantially horizontal line.

16. A method in accordance with claim 15 further comprising programming the offset angle in a monitoring unit to adjust the angle associated with each data set.

17. A method in accordance with claim 15 wherein determining an offset angle comprises calculating a rotation offset angle for the gantry.

18. A computed tomography (CT) system comprising:
    a CT scanner having a rotatable gantry; and
    a monitoring unit for controlling and monitoring the rotation angle of the gantry and configured to receive an offset angle value to adjust the angular labeling at each rotational position of the gantry, the offset angle based on an image of an object scanned by the CT scanner, the object having a substantially flat surface.

19. A CT system in accordance with claim 18 wherein the CT system further comprises a processor configured to compare an image of the substantially horizontal surface of the object obtained by the CT scan and displayed on a display of the CT system with a substantially horizontal line displayed on the display and determine the offset angle for the gantry based on a determined difference of horizontal levelness between the displayed substantially horizontal surface and the displayed substantially horizontal line.

* * * * *